(12) United States Patent
Dretler et al.

(10) Patent No.: US 6,620,172 B1
(45) Date of Patent: Sep. 16, 2003

(54) ENTRAINING BIOLOGICAL CALCULI

(75) Inventors: Stephen P. Dretler, Wayland, MA (US); Paul D. Geragotelis, Sharon, MA (US)

(73) Assignee: MedSource Technologies, Inc., Norwell, MA (US)

( * ) Notice: Subject to any disclaimer, the term of this patent is extended or adjusted under 35 U.S.C. 154(b) by 0 days.

(21) Appl. No.: 09/347,591

(22) Filed: Jul. 1, 1999

(51) Int. Cl.[7] ............................................... A61B 17/22
(52) U.S. Cl. ........................................ 606/128; 606/25
(58) Field of Search .............................. 606/127, 128, 606/25

(56) References Cited

U.S. PATENT DOCUMENTS

| | | | |
|---|---|---|---|
| 843,951 A | 2/1907 | Klock | |
| 2,756,752 A | 7/1956 | Scherlis | |
| 4,271,845 A | * 6/1981 | Chikashige et al. | ........ 606/127 |
| 4,347,846 A | 9/1982 | Dormia | |
| 4,425,908 A | 1/1984 | Simon | |
| 4,793,348 A | 12/1988 | Palmaz | |
| 4,807,626 A | 2/1989 | McGirr | |
| 4,817,600 A | 4/1989 | Herms et al. | |
| 5,037,427 A | 8/1991 | Harada et al. | |
| 5,195,954 A | 3/1993 | Schnepp-Pesch et al. | |
| 5,330,483 A | 7/1994 | Heaven et al. | |
| 5,370,657 A | 12/1994 | Irie | |
| 5,490,859 A | 2/1996 | Mische et al. | |
| 5,626,605 A | 5/1997 | Irie et al. | |
| 5,669,933 A | 9/1997 | Simon et al. | |
| 5,746,767 A | 5/1998 | Smith | |
| 5,895,398 A | * 4/1999 | Wensel et al. | ............... 606/127 |
| 5,989,266 A | * 11/1999 | Foster | ......................... 606/127 |
| 6,156,046 A | * 12/2000 | Passafaro et al. | ............ 606/159 |
| 6,248,113 B1 | * 6/2001 | Fina | ............................. 606/128 |

FOREIGN PATENT DOCUMENTS

| | | |
|---|---|---|
| WO | WO 94/06357 | 3/1994 |
| WO | WO 97/27808 | 8/1997 |
| WO | WO 98/25656 | 6/1998 |
| WO | WO 99/23958 | 5/1999 |

OTHER PUBLICATIONS

Simon & Palestrant, Cardiovasc. Intervent, Radiol., 3:308–316 (1980).
Nakagawa et al., J. of Vascular and Interventional Radiology, 5(3):507–512 (1994).
Simon et al., Radiology, 125:89–94, Oct. 1977.

* cited by examiner

*Primary Examiner*—Paul J. Hirsch
(74) *Attorney, Agent, or Firm*—Hale and Dorr LLP

(57) ABSTRACT

A medical device for entraining biological stones during medical procedures for the fragmentation of urinary, biliary, pancreatic, and other biological calculi and safely removing them from the body. The device includes a guidewire having a longitudinally-extending wire core. A portion of the wire core more adjacent the distal end thereof than the proximal end thereof is wound to form a helical coil which tapers in diameter from a larger diameter end at the proximal end thereof to a smaller diameter end at the distal end thereof. At least a portion of the core forming said helical coil is made of a super-elastic deformable material which collapses upon retraction into a tubular sheath and which reforms into a coil upon deployment from the sheath.

14 Claims, 3 Drawing Sheets

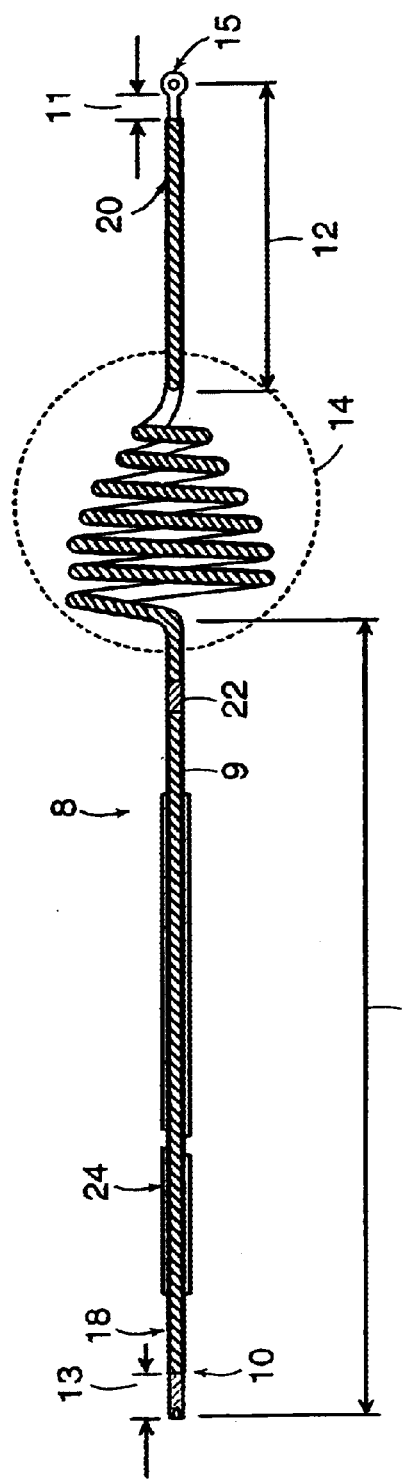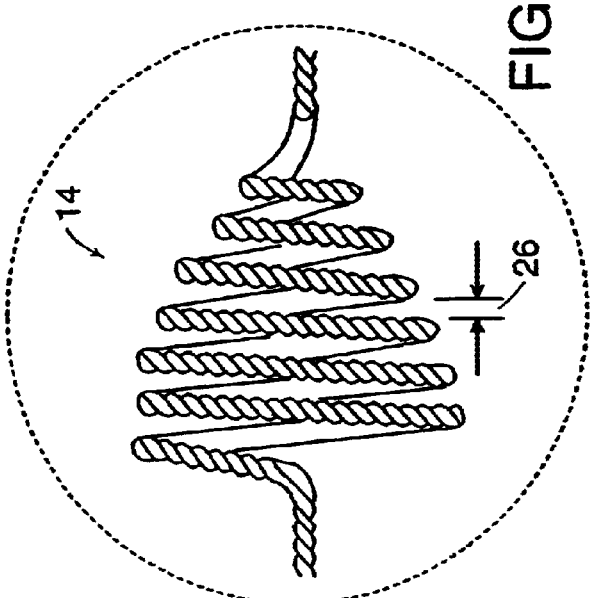

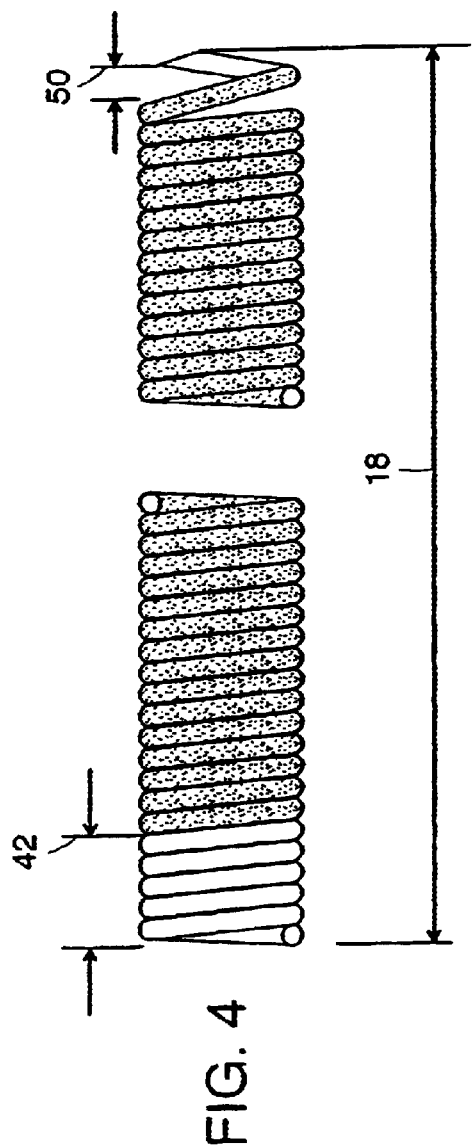
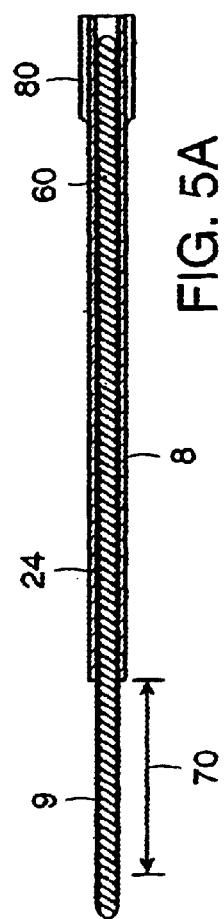
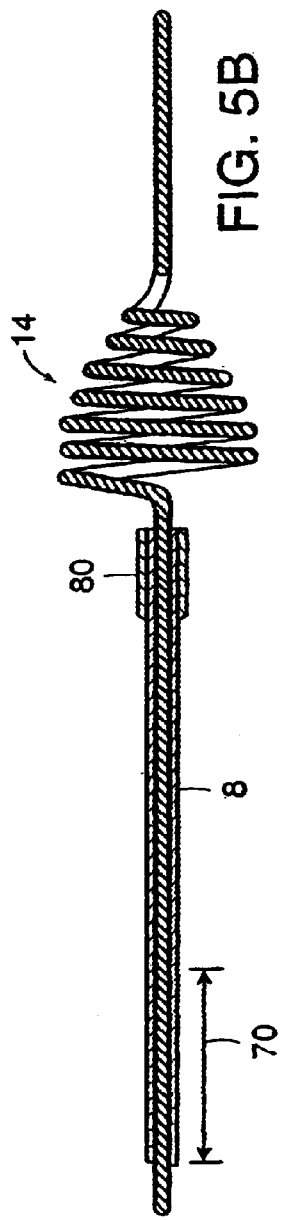

ENTRAINING BIOLOGICAL CALCULI

FIELD OF THE INVENTION

This invention relates to medical treatments for biological concretions and more specifically, to devices and methods for entraining and extracting these concretions such as urinary, biliary, and pancreatic stones, and other calcified material or debris from the body.

BACKGROUND OF THE INVENTION

Urolithiasis, or kidney stone disease, is a significant health problem in the United States. It is estimated that between 2–5% of the general population will develop a urinary calculus during their lifetime. Since being introduced in the 1980s, minimally invasive procedures such as lithotripsy as well as ureteroscopy have become the preferred methods for treatment in a majority of cases of stones in the ureter, and have a potential for application to concretions that develop in other parts of the body such as the pancreas and the gallbladder.

Lithotripsy is a medical procedure that uses energy in various forms such as acoustic shock waves, pneumatic pulsation, electrical hydraulic shock waves, or laser beams to break up biological concretions such as urinary calculi (e.g. kidney stones). The force of the energy, when applied either extracorporeally or intracorporeally, usually in focused and continuous or successive bursts, comminutes a kidney stone into smaller fragments that may be extracted from the body or allowed to pass through urination. Applications to other concretions formed in the body, such as pancreatic, salivary and biliary stones as well as the vascular system, are currently underway in several research laboratories across the United States and Europe.

With the help of imaging tools such as transureteroscopic videotechnology and fluoroscopic imaging, the operator of the lithotripter device can monitor the process of the procedure and terminate treatment when residual fragments are small enough to be voided or grasped and removed. Currently, more than 2000 extracorporeal lithotripter devices and thousands of intracorporeal lithotripter devices are in operation around the world and over five million treatments have been performed.

Although these promising new techniques and instrumentation have improved the treatment of kidney and other biological stones, some problems remain. For example, stones in the ureter which are treated by intracorporeal methods of fragmentation may become repositioned closer to the kidney, and it then becomes necessary to prevent retrograde, i.e. cephalad or upward, migration of the stone fragments toward the kidney. It is also desirable to be able to extract such fragments from the body with the same instrument, preventing the need for successive instrumentation.

The prior art teaches several types of stone extraction devices which are designed to extract biological concretions without the necessity of major open surgery. However, each of these devices suffers from limitations. Most of these devices comprise curved wires which form a cage or basket; see, e.g., U.S. Pat. Nos. 2,943,626, 3,472,230, 4,299,225, 4,347,846, and 4,807,626. The cage or basket-like configuration entrains a single stone within the wire frame; but these prior art devices have rigid frames that lack the maneuverability and flexibility to engage and disengage a stone repeatedly without causing harm to the surrounding tissue, and the entraining portion of these prior art devices are often rigid and are either not collapsible into a smaller configuration or require mechanisms for opening or closing the basket. If the basket or cage of the device itself has become trapped within the ureter, a second device often must be deployed to retrieve the first basket from the body; and if the basket or coil structure has entrained a stone which is too large to be extracted without further fragmentation, it also may be difficult to disengage the stone without a significant amount of manipulation.

Another prior art device comprises one or two inflatable balloon catheters that are manipulated so that the arrested stone is caught between one or more of the balloons. The balloon is slowly withdrawn from the body, and if there are two balloons, the lower balloon acts as a dilator of the ureteral wall and the upper balloon pushes the stone downward towards the bladder. See, e.g., U.S. Pat. No. 4,295,464. The balloons of such devices are difficult to manipulate and failure to maintain the balloons in the correct spatial position may result in loss of the stone. Further, if a stone is caught in a narrow passageway during the extraction process, the balloon catheters cannot move the stone away from the exit direction to dislodge it from the passageway; and if the stone is caught in between the lining of the ureteral wall and the balloon, the pressure of the balloon may push the stone into the lining, causing significant damage to the lining. Also, soft air-inflated balloons are easily punctured when used in conjunction with most types of stone fragmentation procedures.

There is a particular need, therefore, for a guidewire device that prevents upward migration of stone fragments generated during a stone fragmentation procedure, and which safely and efficiently extracts fragments from the body. Thus, a device possessing the following abilities is desired: ability to act as an energy-absorbing barrier that prevents fragments from migrating toward the kidney; ability to "sweep" one or multiple smaller fragments downward and out of the body; the ability to engage and disengage the stone repeatedly, and the ability to disengage the stone for repositioning for further fragmentation if the entrained stone is too large to pass from the body.

SUMMARY OF THE INVENTION

Accordingly, it is an object of the present invention to provide a flexible, form-fitting device which prevents upward migration of biological stones and fragments of stones generated during medical procedures for stone fragmentation. It is another object of the invention to provide a device in which the entraining configuration may be collapsed and redeployed repeatedly as required during a stone fragmentation procedure.

A further object of the invention is to provide a device which can safely guide the one or multiple stone fragments from the body, sweeping it downward and which as a safety feature, disengages itself from a stone that is too large to pass a specific path in the body by a simple pulling motion.

The invention features a device comprising a wire core at least a portion of which is comprised of a super-elastic deformable material wound to form a helical coil which tapers from a larger diameter proximal end to a smaller diameter distal end. Because the coil portion of the core is formed of a super-elastic material, preferably a nickel titanium alloy such as nitinol, the coil has the ability to uncoil into a relatively straight configuration when retracted into a tubular sheath or pulled against an obstruction, and reform into a coil configuration when deployed, e.g. withdrawn from, a tubular sheath. In preferred embodiments, a continuous super-elastic wire core is surrounded by a wrapped helical spring, typically having two sections which are attached to each other and to the core at a midjoint proximal to the tapered helical coil. Another preferred embodiment features a layer of polymeric material covering the surface at least a portion of the device, as well as a layer of radiopaque material which covers at least a portion of the tubular sheath and/or the device.

BRIEF DESCRIPTION OF THE DRAWINGS

FIG. 1 generally shows one preferred embodiment of the claimed device for a urinary application.

FIG. 1A is an enlarged view of the tapered helical coil portion of the device of FIG. 1.

FIG. 4 is a detailed schematic of a wrapped helical spring 18 of FIG. 3, a portion of which has been stretched so that gaps are introduced between adjacent turns of the spring.

FIGS. 5A and 5B are profile views of the device of FIG. 1, respectively illustrating the helical coil of the device withdrawn into, and fully deployed (i.e. withdrawn) from the sheath.

DETAILED DESCRIPTION OF THE PREFERRED EMBODIMENT

Figure 2:
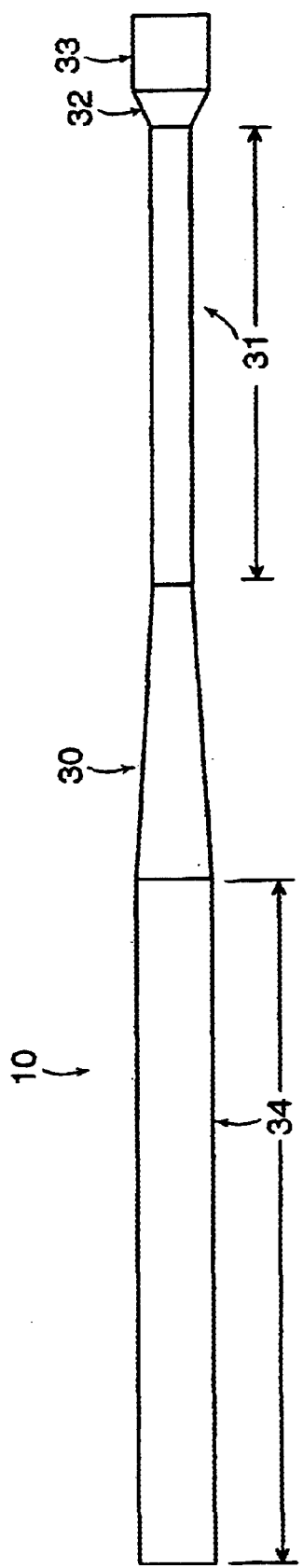
FIG. 2 is a schematic view of the wire core of the device of FIG. 1.

With reference to FIGS. 1 and 1A, a medical device 8 embodying the present invention includes a wire core 10 having a super-elastic, tapered helical coil portion 14 adjacent but spaced a short distance from its distal end 11. Except at its extreme ends, wire core 10 is surrounded by two wrapped helical springs 18, 20, which in turn are covered with a layer of a polymeric material. Hereinafter, the wire core 10, the helical spring(s) surrounding the core, and the layer of polymeric material (if any) may be collectively referred to as the guidewire 9. As shown in FIG. 1, a portion of the guidewire 9 proximal to the helical coil section 14 is surrounded by an axially-movable tubular sheath 24. The distal end 11 and the proximal end 13 of the wire core 10 are rounded; typically a hemispherical tip 15 is bonded to the distal end 11. It will be appreciated that FIG. 1 is not to scale; the overall length of the device is over one hundred times its maximum diameter.

The overall length of guidewire 9 (and thus that of wire core 10) depends on the application for which the device is intended. Generally the overall length will be in the range of about 50 to about 250 cm. For urinary applications, the total length of the device is preferably about 140–220 cm, and most preferably about 200 cm. Devices for other applications, or those intended for use with children, will be of different lengths.

As described below, wire core 10 preferably has a tapered cross-section. The maximum diameter of the wire core 10 itself is typically in the range of about 0.015 inches to 0.04 inches, and preferably is about 0.020 inches. The overall diameter of the guidewire 9 is slightly greater, e.g., in the preferred embodiment, it is about 0.038 inches and may, depending on the particular device, vary from about 0.018 to 0.05 inches.

The helical coil section 14 of wire core 10 has a maximum diameter at its proximal end, and a minimum diameter at its distal end. The smaller diameter, i.e., the distal end of coil 14 is spaced a relatively short distance 12 (e.g., about 2 cm to about 50 cm, preferably about 10–24 cm, most preferably about 14 cm) from the distal end 11 of device 8. The portion 16 of core 10 proximal of the helical coil section 14 is about 50 cm to about 200 cm long; the overall length is usually not critical and, like many of the other particular dimensions of the device, depends on the intended use. Typically, the length of the proximal portion 16 of the core wire 10 is about 100 to 130 cm, and preferably about 120–130 cm.

The particular number of turns, the maximum diameter, and the length of the tapered helical coil section 14 depends, again, on the intended use of device 8. Typically, the coil has between about 5 and 15 turns, and preferably about 7 to 10 turns. Its maximum diameter, at the proximal end of the helical coil section 14 is in the range of about 0.2 cm to 3.0 cm; and for usual applications is about 0.5–1.5 cm, and most preferably is about 0.7–0.8 cm. The overall length of the coil depends, of course, on such things as the wire size and number of turns, but typically is in the range of about 0.5 cm to about 3.0 cm; and for most applications is preferably about 1.5 cm. Adjacent turns of the coil may abut each other. Typically, and as best shown in FIG. 1A, there may be small gaps 26, up to about 2 mm wide, between the adjacent wire turns forming the tapered helical coil. As will be discussed in detail later, at least the portion of the wire core 10 forming the tapered helical section is made of a super-elastic material, and the above dimensions are those of the coil when it is in its set, or fully deployed, configuration, as shown in FIG. 1.

A pair of wrapped helical springs 18, 20 surround essentially the entire length of wire core 10, except for relatively short (i.e., less than 0.050 inch long) regions at the extreme distal end 11 and proximal end 13. One of the springs, designated 18, tightly surrounds the portion of the wire core 10 extending from adjacent the proximal end 13 of the core 10 to a region 22 a short distance proximal of the tapered helical coil section 14. A second wrapped helical spring 20 tightly surrounds the portion of the wire core 10 (including the helical spring portion 14) extending distally from region 22 to adjacent the distal end 11 of the wire core 10.

Preferably, the helical spring 18 has a length of about 150–180 cm, most preferably about 160 cm, and the helical spring 20 has a length of about 10–50 cm, most preferably about 40 cm. The adjacent ends of the are attached both to each other and to the surrounded core 10 at region 22, herein referred to as a midjoint or midjoint region, proximal of the helical coil section 14. Preferably, the midjoint has a length of about 0.02 to 0.06 inches, most preferably about 0.03–0.04 inches. It is also preferred that the two springs are wrapped in the same direction, e.g., right-hand wrapped, and the turns at what will be the adjacent ends of the two springs are slightly stretched, so that the turns of the springs at midjoint 22 can be coiled one into the other, interlocking in a fashion similar to that of a finger joint. Preferably, about 0.5 to 2 turns of the adjacent ends of the two springs are stretched and interlocked with one another. FIG. 4 illustrates a stretched turn having gaps 50 between adjacent turns of spring 18.

These inter-connected turns are further attached to each other and to the wire core 10, typically with an adhesive that can form a high-strength bond with a wide variety of substrates, particularly metal and polymeric materials. Once the adhesive is applied, it typically is cured by a conventional curing method, such as heat setting and air-drying. It is preferred that the adhesive comprise epoxy, preferably a UV curing adhesive that offers a secondary heat cure capability to allow areas shadowed from ultraviolet light to be cured with heat, such as that identified by the trade name Dynam 128-M-VT. In some other embodiments, other means of attachment may be employed, preferably welding or brazing.

In the preferred embodiment, spring 18 is wound from a larger diameter wire than is spring 20; e.g., proximal spring 18 is wound from wire having a diameter of about 0.008 in while the wire from which distal spring is wound has a diameter of about 0.004 in. It has been found that a larger diameter proximal helical spring 18 provides the proximal portion of the device 8 with greater rigidity and column strength; and that the use of a smaller diameter distal helical spring 20 provides the distal portion of the device with greater flexibility. In other embodiments, however, the arrangement may be somewhat different. For example, both the distal and proximal springs may have the same diameter, or only a single spring extending substantially the entire length of the wire core may be used. Regardless of the number of springs or their diameters, the springs may be made of a wide range of materials; and the springs are wound so that their outer diameters do not exceed the desired outer diameter, e.g., 0.038 inches, of the guidewire. Typically the springs are made of stainless steel.

FIG. 2 shows the construction of the wire core 10, which, in the preferred embodiment, is a commercially available NiTiCr (55.73%Ni, 44.04Ti, 0.22%Cr, and less than 0.05% C and O) superelastic wire having, as supplied, a diameter of 0.020 inches. As shown the wire has been ground so that, in addition to full diameter sections 33 and 34 adjacent, respectively, its distal and proximal ends, it includes a pair of tapered portions 30, 32 on opposite sides of a smaller diameter portion 31. The long full diameter section 34 extending from the proximal end of the core wire, and the longer tapered portion 30, provide desired column strength in the portion of the core wire proximal of the smaller diameter portion 31. Preferably, the long full diameter section 34 has a length of about 130–200 cm, most preferably about 150 cm and a diameter of about 0.02 inches. Preferably, the smaller diameter portion 31 has a length of about 20–40 cm, most preferably about 30 cm and most preferably a diameter of about 0.009 inches. The longer tapered portion 30 is preferably about 5–10 cm in length, most preferably about 8 cm, and the shorter tapered portion 32 preferably has a length of about 0.01 to 0.05 inches, most preferably 0.025 inches. The shorter full diameter section 33 preferably has a length of about 0.1 to 0.5 inches, most preferably about 0.2 inches.

The smaller diameter portion 31, which as discussed above, forms helical coil 14. Typically, the lengths of springs 18, 20 are such that the midjoint region 22 of core 10 is part of smaller diameter portion 31. The smaller diameter portion 31 of the core wire 10 immediately distal of the helical coil provides the flexibility required for various applications involving the entraining and removal of biological calculi.

In the preferred embodiment, the entire wire core 10 is a continuous piece of super-elastic wire; in other embodiments, the portion of the core wire 10 that will form helical coil 14 will be superelastic, but other portions of the core wire, e.g., the full diameter section 34 and tapered portion 30, may be stainless steel. A number of superelastic NiTi alloys, commonly referred to as nitinol, are available commercially.

The helical coil portion 14 of core wire 10 is formed by wrapping the smaller diameter portion 31 around a mandrel to form it into the desired conical shape, and then heating it at sufficient time and temperature (the particular time and temperature depend on the particular superelastic material and are conventional) to set the conically-shaped coil in the core wire. As is well-known in the art, once the portion of the core wire forming coil 14 has been heat-treated to set the desired tapered helical coil configuration, the coil may be drastically deformed (e.g., by pulling the core wire portions on either side of the coil to straighten the wire turns forming the coil) but will return to its set tapered coil configuration when released. It will be apparent that these deformation/reconformation characteristics are important to the use of the medical device. They also assist in the device's construction, e.g., by permitting the core wire to be straightened so that helical spring 20 may more easily be slid over the distal portion of the core wire, over the portion of the wire that forms coil 14, to midjoint region 22.

Figure 3:
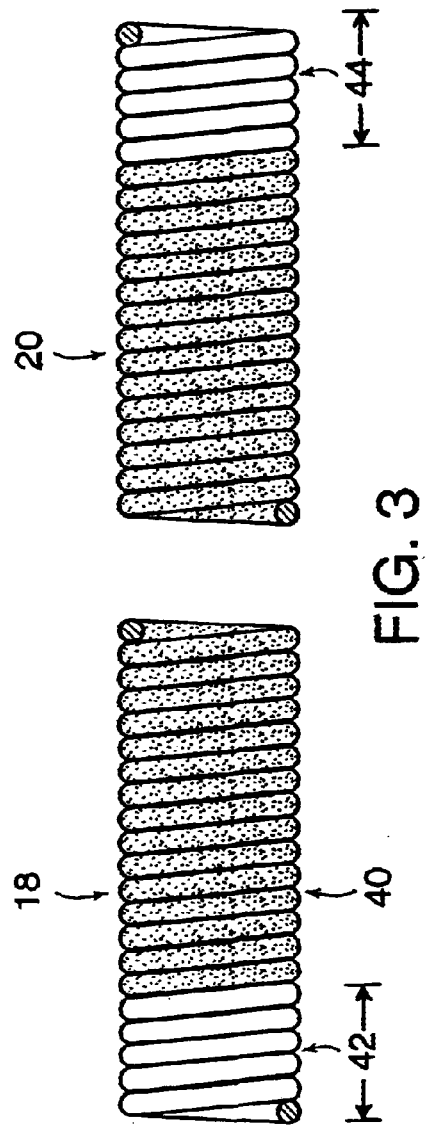
FIG. 3 is a schematic view of two wrapped helical springs generally coated with a polymeric material.

As discussed above, in the preferred embodiment of the invention, a helical spring covers most of the length of the core wire 10. In other embodiments, the use of such a spring may be omitted. In either event, a low-friction layer of polymeric material preferably covers the outer surface of the device, i.e., the outer surface of the core wire when no spring is used or, if the core wire is wrapped with one or two helical springs, the outer surface of the spring(s). FIG. 3 illustrates a wrapped helical spring 18 which has been covered, typically by spray-coating, with a layer of polymeric material 40. As will be noted, the coating 40 does not cover small lengths 42, 44 at the proximal and distal ends of spring 18..

Although any of a wide range of low-friction materials may be used to form the coating 40, the coating of the preferred embodiment is a fluorinated polymer, e.g., polytetrafluoroethylene, one type of which is sold by duPont de Nemours Co. under the trademark TEFLON. In some embodiments, various portions of the device are coated with polymeric materials of different colors. For example, as shown in FIGS. 5A and 5B, a colored portion 70 of core 10 that is at least as long in length as the length of the helical coil 14 may be coated with a polymeric material of a color different than that of the rest of the device proximal and/or distal of it; or in some embodiments may be left uncolored or uncoated. As will be apparent, providing a colored portion 70 that possesses a color different from that of the rest of the device assists a user in determining whether the tapered helical coil is within or without sheath 24. Thus, when the coil has been retracted into the sheath 24, the colored portion 70 will be visible to the user. When the coil has been withdrawn outside the sheath 24 (i.e. deployed), the colored band 70 will no longer be visible to the user.

Sheath 24 has a length that is less than the overall length of guidewire 9, but is considerably more than the length of wire core 10 forming the helical spring portion 14 so that a physician using device 8 can grasp the proximal end of the sheath when the device has been properly positioned within a patient. The inner diameter of sheath 24 is slightly greater than that of the diameter of the wrapped spring that surrounds helical spring portion. Its outer diameter depends, principally, on the wall thickness and strength required to retain the portion of wire core 10 forming spring 14 in a relatively straight configuration when the helical coil spring is drawn into the sleeve, i.e. sheath 24. For example, in the preferred embodiment, sheath 24 is 75 cm long, has an inner diameter of 0.043 inches and an outer diameter of 0.066. The material of which the sheath is made also must be somewhat flexible, so that the sheath can be introduced into the body along with the rest of the device. In the preferred embodiment, the sheath is made of a flexible polymeric material such as that sold under the trade name PEBAX, and its distal portion is covered with a radiopaque material 80 to assist a user in locating the distal end of the sheath during a medical procedure.

FIGS. 1 and 5B illustrate device 8 with sheath 24 positioned proximally of helical coil portion 14. As will be appreciated, in this relatively positioning of the coil and sheath, the helical coil portion 14 is unconstrained and conforms to the tapered, helical configuration in which the nitinol (or other superelastic material) forming the coil portion was heat set. FIG. 5A illustrates device 8 with the sheath 24 and helical coil portion 14 moved axially relative to each other so that the helical coil portion has been retracted into the sheath. As shown, the super-elastic qualities of the material forming the coil portion permit it to be deformed into an essentially straight configuration 60, in which the coil portion of guidewire 9 fits into the sheath whose inner diameter is only slightly (e.g., in the preferred embodiment about 0.005 inches) greater than the outer diameter of the wrapped wire core. If the super-elastic portion of the coil wire that has been set in the helical coil configuration is then withdrawn from sheath 24, e.g., by moving the sheath proximally relative to the core wire (or the core wire distally relative to the sheath), it will reform the tapered helical spring configuration shown in FIG. 5B.

In use, device 8 is provided to a physician performing the desired medical procedure, e.g., a lithotripsy to remove kidney stones from a patient's ureter, in the configuration shown in FIG. 5A, with sheath 24 surrounding the helical coil portion 14 of the guidewire 9. The sheathed guidewire is then introduced into the patient's urinary passage, typically with its progress being monitored in the conventional manner, until the radiopaque distal portion 80 of sheath 24 is slightly beyond the location of the stone or other biological calculus lodged in the ureter. With the sheath held in place, the guide wire is then advanced so that the portion of the guidewire forming helical coil portion 14 is deployed distally from sheath 24 and forms the tapered, helical coil configuration, occluding the passageway.

Preferably, the diameter of the largest portion of the helical coil portion 14, in its fully deployed configuration (e.g., the configuration in which it was set during manufacture) is the same or slightly greater than that of the hollow passage (e.g., the ureter) in which the coil will be deployed in the course of a medical procedure. This insures that the outer diameter of the coil will conform to the size of the passage and occlude it efficiently, preventing migration of the kidney store or other calculus.

With the coil thus deployed, energy is applied to the stone or other calculus, in the same manner as in conventional lithotripsy, to break the stone into smaller fragments that may either be extracted or allowed normally to pass from the body. During the fragmentation procedure, the deployed coil functions as a physical barrier, trapping the larger stone or calculus fragments either within the coiled structure or proximal to the coil. The smaller fragments, e.g., those that are able to pass between the turns of the helical coil 14, are typically of such size that they can pass normally from the body. The super-elasticity of the material forming the coil, particularly when combined with the tapered configuration, provides a flexible barrier that is able to absorb the kinetic energy of the fragments produced when a laser or other energy is used to comminute or ablate the calculus.

In some procedures, the deployed coil can be used as a "basket," to capture the fragments and permit them to be withdrawn from the body by withdrawing the guidewire 9 with the helical coil portion in its deployed configuration. In other procedures, the deployed coil is retracted back into sheath 24, and then repositioned for further deployment.

The following examples will further illustrate the invention. These examples are not intended, and should not be interpreted, to limit the scope of the invention.

EXAMPLE I

The device was tested in vitro under conditions that simulated the ureter and utilizing various particles that simulated stone fragments. The test ureter consisted of a clear plastic tube having an inner diameter of about 10 mm with openings to introduce particles and the device. A pump with a flowrate of 1L/min was connected to the test device to simulate the high intensity with which fragmentary debris generated during lithotripsy will flow into the tapered helical coil that has been deployed within the ureter.

Four different kinds of particles were used to simulate stone fragments:

1) Crushed walnut shells: various jagged shaped (about 2 mm at its greatest length).

2) Zircon oxide beads: spheroidal beads (about 2.0 to 2.5 mm in diameter).

3) Steel ball bearings: spheroidal balls (about 4.7 mm diameter)

4) Plastic beads: spheroidal balls (about 1/8 inches diameter).

The test was conducted by introducing the device and deploying it within the clear plastic tube. The particles were then introduced into the water stream flowing into the tube. The device successfully collected all of the tested particles.

EXAMPLE II

In another series of experiments, the same equipment described above was used. In addition, actual kidney stones were used as test particles along with the simulated fragments listed above. A lithotripter, specifically CALCUS-PLIT Model #276300 (Storz) was used to fragment the stone that was entrained within the cone of the tapered helical coil. The coil secured the stone while a probe of the lithotripter device fragmented it. Tables 1 and 2 provide the results of these preliminary experiments and provide information about the sizes and weight of fragmented debris collected and passed by the device during a laser lithotripsy procedure.

TABLE I

With Stone Stopper

| Sample | Stone Type | Stone Size & Weight Before Breaking* | Size & Weight of Debris Passed* | Size & Weight of Debris Captured* |
| --- | --- | --- | --- | --- |
| 1A | Uric Acid | 6.34 mm/ 1.42 gm | 4 mm/>.01 gm | 4 mm/.03 gm |
| 1B | Uric Acid | 6.31 mm/ 1.34 gm | 3.5 mm/.01 gm | 5.5 mm/.07 gm |
| 2A | Uric Acid | 6.26 mm/ 1.43 gm | 3 mm/>.01 gm | 3 mm/.07 gm |
| 3A** | Struvite/ Apatite | 6.71 mm/ 1.31 gm | 1 mm/.01 gm | 2 mm/>.01 gm |
| 4A*** | Cystic (hard) | 6.64 mm/ 1.42 gm | 4 mm/>.01 gm | 3.5 mm/.02 gm |
| 5A | Black | 6.55 mm/ 1.29 gm | 1 mm/>.01 gm | 2.5 mm/>.01 gm |

*Size is determined by the largest measured dimension of the particle.
**Debris comprises fine and powdery grains.
***Stone ablated using laser lithotripsy.

TABLE 2

| Debris Type | Size of Debris & No. of Pieces* | Size of Debris & No. of Pieces Not Entrained* | Weight of Debris Not Entrained |
|---|---|---|---|
| Kidney Stone (Struvite, soft) | ~8 mm dia./1 pc. | <.5 to 3 mm /20 to 25 pcs. | .05 grams |
| Kidney Stone (hard) | ~8 mm dia./1 pc. | ~6 mm/1 pc. | .10 grams |
| Walnut Shell | 2.8–3.9 cm/16 pcs. | None passed | None passed |
| Walnut Shell | 2.8–3.9 cm/4 pcs. | None passed | None passed |

*For determining the size of the debris, the largest measurement of the irregular shape was recorded.

The deployed cone containing the particulate matter was then pulled downward (i.e. in the proximal direction with respect to the device) a distance of 15 cm to simulate extraction of stones entrained within the coil. It was observed that when fragments of a diameter greater than about 4 mm were entrained in the tapered helical coil, the coil that held the larger fragment could not be pulled through the plastic tube. The larger fragment's resistance to the pulling force of the user caused the coil to unwind, letting go of the fragment. The device was then withdrawn into the sheath and advanced beyond the fragment. Further fragmentation was conducted, and the smaller fragments were then extracted from the test tubing. It was appreciated that the unwinding feature of the coil upon pulling against an obstruction provides a desirable safety mechanism, whereby the user is prevented from trying to extract a stone that is too large for the particular passageway, and thus avoiding injury to the ureter. The results of the "pulling test" are provided in Table 3

TABLE 3

| Debris Type | Size of Debris & No of Pieces* | Weight of Debris | Distance Pulled |
|---|---|---|---|
| Kidney Stone (Struvite, soft) | 6 mm/2 pieces | .10 grams | 15 cm |
| Walnut Shell | 2.8–3.9 cm/4 pieces. | .08 grams | 15 cm |
| Walnut Shell | 2.8–3.9 cm/16 pieces | .30 grams | 15 cm |

*For determining the size of debris, the largest measurement of the irregular shape is recorded.

The various technical and scientific terms used herein have meanings that are commonly understood by one of ordinary skill in the art to which the present invention pertains. As is apparent from the foregoing, a wide range of suitable materials and/or methods known to those of skill in the art can be utilized in carrying out the present invention; however, preferred materials and/or methods have been described. Materials, substrates, and the like to which reference is made in the foregoing description and examples are obtainable from commercial sources, unless otherwise noted. Further, although the foregoing invention has been described in detail by way of illustration and example for purposes of clarity and understanding, these illustrations are merely illustrative and not limiting of the scope of the invention. Other embodiments, changes and modifications, including those obvious to persons skilled in the art, will be within the scope of the following claims.

What is claimed is:

1. A medical device comprising a generally longitudinally-extending wire core having a shaped construction wherein the wire core contains at least one tapered portion and portions of differing cross-sectional diameters, wherein a portion of said core more adjacent the distal end thereof than the proximal end thereof being wound to form a helical coil which tapers in diameter from a larger diameter end at the proximal end thereof to a smaller diameter end at the distal end thereof, at least the portion of said core forming said helical coil being made of a super-elastic deformable material, including a wrapped helical spring surrounding a longitudinally-extending portion of said core.

2. The medical device of claim 1, wherein said spring surrounds a major fraction of the overall length of said core.

3. The medical device of claim 1, wherein the distal and proximal ends of said spring are attached to said core.

4. The medical device of claim 1, wherein said spring includes a first spring portion surrounding a first longitudinally-extending portion of said core and a second spring surrounding a second longitudinally-extending portion of said core, said second longitudinally-extending portion including said helical coil, said portions being adjacent to one another, and adjacent ends of said spring portions being attached to each other and to said core in a region proximal of said helical coil.

5. The medical device of claim 4, wherein the first spring portion and said second spring portion comprise wires of different diameters.

6. The medical device of claim 1, wherein the spring comprises stainless steel.

7. The medical device of claim 1, wherein a layer of a polymeric material substantially covers the outer surface of said spring.

8. The medical device of claim 7, wherein the polymeric material comprises a fluorinated polymer.

9. The medical device of claim 8, wherein the fluorinated polymer is polytetrafluoroethylene.

10. The medical device of claim 3, wherein the distal and proximal ends of said spring are attached to said core by a weld or braze.

11. The medical device of claim 4, wherein the adjacent ends of said first and second spring sections are attached-to each other and to said core by an epoxy.

12. The medical device of claim 11, wherein the epoxy comprises epoxy which cures upon exposure to ultraviolet radiation.

13. A medical device comprising:
    a generally longitudinally-extending wire core having a shaped construction wherein the wire core contains at least one tapered portion and portions of differing cross-sectional diameters, wherein, a portion of said core more adjacent the distal end thereof than the proximal end thereof being wound to form a helical coil which tapers in diameter from a larger diameter end at the proximal end thereof to a smaller diameter end at the distal end thereof, at least the portion of said core forming said helical coil being made of a super-elastic deformable material; and,
    a pair of wrapped helical springs surrounding the wire core, one of said springs extending distally from a point adjacent the proximal end of said core, the other of said springs extending proximally from a point adjacent the distal end of said core to a point proximal to said helical coil, one end of one of said springs being connected to one end of the other of said springs and to said core, and the other end of each of said springs being connected to the core.

14. The medical device of claim 13, wherein a portion of the coil is covered with a radiopaque material.

* * * * *

UNITED STATES PATENT AND TRADEMARK OFFICE
CERTIFICATE OF CORRECTION

PATENT NO.    : 6,620,172 B1
DATED         : September 16, 2003
INVENTOR(S)   : Dretler et al.

It is certified that error appears in the above-identified patent and that said Letters Patent is hereby corrected as shown below:

<u>Title page,</u>
Item [73], Assignee, please replace "Medsource Technologies, Inc." with -- The MicroSpring Company LLC, Norwell, MA --.

Signed and Sealed this

Eighteenth Day of May, 2004

JON W. DUDAS
*Acting Director of the United States Patent and Trademark Office*